US011883467B2

(12) United States Patent
Olshansky et al.

(10) Patent No.: US 11,883,467 B2
(45) Date of Patent: Jan. 30, 2024

(54) INSULIN FORMULATIONS AND METHODS OF USING SAME IN PRETERM INFANTS

(71) Applicant: Elgan Pharma Ltd, Nazareth (IL)

(72) Inventors: Michal Olshansky, Tel Aviv (IL); Elena Ostrovsky, Rishon-LeZion (IL); Stav Zeldis, Herzeliya (IL)

(73) Assignee: Elgan Pharma Ltd, Nazareth (IL)

( * ) Notice: Subject to any disclaimer, the term of this patent is extended or adjusted under 35 U.S.C. 154(b) by 0 days.

(21) Appl. No.: 17/903,074

(22) Filed: Sep. 6, 2022

(65) Prior Publication Data

US 2023/0000953 A1 Jan. 5, 2023

Related U.S. Application Data

(63) Continuation of application No. PCT/IL2022/050371, filed on Apr. 11, 2022.

(60) Provisional application No. 63/173,442, filed on Apr. 11, 2021.

(51) Int. Cl.
| | |
|---|---|
| *A61K 38/28* | (2006.01) |
| *A61P 3/02* | (2006.01) |
| *A61K 9/00* | (2006.01) |
| *A61K 9/16* | (2006.01) |
| *A61K 9/19* | (2006.01) |

(52) U.S. Cl.
CPC ............ *A61K 38/28* (2013.01); *A61K 9/0095* (2013.01); *A61K 9/1611* (2013.01); *A61K 9/1652* (2013.01); *A61K 9/1694* (2013.01); *A61K 9/19* (2013.01); *A61P 3/02* (2018.01)

(58) Field of Classification Search
CPC .... A61K 38/28; A61K 9/0095; A61K 9/1611; A61K 9/1652; A61K 9/1694; A61K 9/19; A61P 3/02
See application file for complete search history.

(56) References Cited

U.S. PATENT DOCUMENTS

| | | | | |
|---|---|---|---|---|
| 6,685,967 B1 * | 2/2004 | Patton | ....................... | A61P 5/50 424/45 |
| 7,351,798 B2 * | 4/2008 | Margolin | ............... | A61K 47/40 424/501 |
| 2003/0148925 A1 * | 8/2003 | Kampinga | ............. | A61K 38/28 514/53 |
| 2011/0182946 A1 * | 7/2011 | Johnston | ............... | A61K 9/5161 977/773 |
| 2021/0008171 A1 | 1/2021 | Safonov | | |

FOREIGN PATENT DOCUMENTS

| | | |
|---|---|---|
| RU | 2288000 | 11/2006 |
| WO | WO 2020/012040 | 1/2020 |
| WO | WO 2020/240558 | 12/2020 |
| WO | WO 2022/219625 | 10/2022 |

OTHER PUBLICATIONS

Kadima et al., The influence of ionic strength and pH on the aggregation properties of zinc-free insulin studied by static and dynamic laser light scattering. Biopolymers 1993, 33(11):1643-1657. (Year: 1993).*
International Search Report and the Written Opinion dated Jul. 7, 2022 From the International Searching Authority Re. Application No. PCT/IL2022/050371. (23 Pages).
Beardsall et al. "A Randomised Controlled Trial of Early Insulin Therapy in Very Low Birth Weight Infants, 'Nirture' (Neonatal Insulin Replacement Therapy in Europe)", BMC Pediatrics, 7(1): 29-1-29-10, Aug. 10, 2007.
Cold Spring Harbor "Phosphate-Buffered Saline PBS", Cold Spring Harbor Protocols, Table. 2006.
Hwang et al. "Use of Insulin Glargine in the Management of Neonatal Hyperglycemia in ELBW Infant", Pediatrics, 141(Suppl. 5): S399-S403, Apr. 1, 2018.
Kreznar et al. "Host Genotype and Gut Microbiome Modulate Insulin Secretion and Diet-Induced Metabolic Phenotypes", Cell Reports, 18(7): 1739-1750, Feb. 14, 2017.
Lemas et al. "Alterations in Human Milk Leptin and Insulin are Associated With Early Changes in the Infant Intestinal Microbiome", The American Journal of Clinical Nutrition, 103(5): 1291-1300, Published Online Mar. 8, 2016.
Ménard et al. "Insulin Accelerates the Development of Intestinal Brush Border Hydrolytic Activities of Suckling Mice", Developmental Biology, 85(1): 150-155, Jul. 15, 1981.
Ou et al. "Nutrition in Necrotizing Enterocolitis and Following Intestinal Resection", Nutrients, 12(2): 520-1-520-16, Feb. 18, 2020.
Shulman "Effect of Enteral Administration of Insulin on Intestinal Development and Feeding Tolerance in Preterm Infants: A Pilot Study", Archives of Disease in Childhood Fetal and Neofetal Edition, 86(2): F131-F133, Mar. 2002.
International Preliminary Report on Patentability dated Oct. 26, 2023 From the International Bureau of WIPO Re. Application No. PCT/IL2022/050371 (10 Pages).

\* cited by examiner

*Primary Examiner* — Robert A Wax
*Assistant Examiner* — Olga V. Tcherkasskaya

(57) ABSTRACT

An insulin formulation and a method of preparing and using same. The insulin preparation includes insulin, oligosaccharide and sodium chloride at a ratio of 1:A:B (w:w:w respectively) with ranges of A and B are 1000-5000 and 10-50, respectively.

9 Claims, 9 Drawing Sheets

INSULIN FORMULATIONS AND METHODS OF USING SAME IN PRETERM INFANTS

RELATED APPLICATIONS

This application is a Continuation of PCT Patent Application No. PCT/IL2022/050371 having International filing date of Apr. 11, 2022, which claims the benefit of priority under 35 USC § 119(e) of U.S. Provisional Patent Application No. 63/173,442 filed on Apr. 11, 2021. The contents of the above applications are all incorporated by reference as if fully set forth herein in their entirety.

FIELD AND BACKGROUND OF THE INVENTION

The present invention relates to insulin formulation formulated for use in infant feed. Embodiments of the present invention relate to methods of preparing insulin and an infant feed including same and to methods of using the insulin-containing infant feed in preventing or reducing severity of pre-term infant disorders such as late onset sepsis or necrotizing enterocolitis/colitis/enterocolitis.

Birth is considered premature, or preterm, when it occurs before the 37th week of pregnancy. The final weeks in the womb are crucial for healthy weight gain and for the full development of various vital organs.

Human milk is recognized as the optimal feeding for all infants including pre-term infants because of its proven health benefits to infants.

Human milk contains a substantial number of hormones and growth factors and studies have shown that some of these hormones (e.g. insulin, insulin-like growth factor 1, IGF-1, epidermal growth factors) have an effect on the small intestine following oral administration.

Studies have also shown that that addition of insulin to preterm infant formulas results in better growth and accelerated intestinal maturation [Shulman, R. J., 2002; Archives of Disease in Childhood-Fetal and Neonatal Edition, 86(2), F131-F133].

"Insulin-containing infant feed formulations have been previously described. However, when infants are born prematurely, their digestive systems may not be fully developed and as a result, many of these pre-term infants experience feeding difficulties and disorders that directly or indirectly relate to malnourishment."

Late-onset sepsis (LOS), defined as sepsis onset after 72 h of life, is a leading cause of mortality in the neonatal intensive care unit. The incidence rates for LOS in preterm infants vary between 20 and 38% in the first 120 days of life, and mortality rates range from 13 to 19%.

Necrotizing enterocolitis (NEC) is a disease that affects mostly the intestine of premature infants. The wall of the intestine is invaded by bacteria, which cause local infection and inflammation that can ultimately destroy the wall of the intestine. About 7% of pre-term infants develop necrotizing enterocolitis and among those affected, about 25% die.

While reducing the present invention to practice, the present inventors have formulated an insulin formulation that can be solubilized in an infant feed (formula or breast milk) and have shown for the first time that such a feed formulation can be used to prevent, or reduce the severity of LOS and NEC.

SUMMARY OF THE INVENTION

According to one aspect of the present invention there is provided a method of preparing insulin for use in an infant feed comprising: solubilizing insulin in hydrochloric acid to obtain solubilized insulin; and diluting the solubilized insulin with water and adjusting a pH to 6.9-8.0.

According to embodiments of the present invention the method further comprises adding cyclodextrin to solution (b) to thereby encapsulate the insulin in cyclodextrin cavities; and adjusting pH to 6.9-8.0.

According to embodiments of the present invention the method further comprises compounding a result of (b) or (d) with a sodium chloride solution and a maltodextrin solution and adjusting the pH to 6.7-7.6.

According to embodiments of the present invention the composition is combined with an oil-in-water nanodroplets emulsion wherein the nanodroplets include the Docosahexaenoic acid (DHA) and the coenzyme Q10.

According to embodiments of the present invention the method further comprises filtering a result of the compounding and lyophilizing a filtrate to obtain an amorphous powder with a pH 6.0-7.6

According to another aspect of the present invention there is provided a method of producing an infant feed with insulin comprising reconstituting the amorphous powder described herein in the infant feed.

According to another aspect of the present invention there is provided an insulin formulation comprising insulin, oligosaccharide and sodium chloride at a ratio of 1:A:B (w:w:w respectively), wherein ranges of A and B are 1000-100,000 and 10-50, respectively.

According to embodiments of the present invention the insulin formulation has a pH of 6.0-7.6 when reconstituted in deionized water or 0.9% sodium chloride solution at concentration of 0.03 g/ml.

According to embodiments of the present invention the insulin formulation further comprises cyclodextrin.

According to embodiments of the present invention the cyclodextrin is at a ratio of 10-1000 with respect to the insulin.

According to embodiments of the present invention 1 gram of the insulin formulation includes 2-40 IU.

According to another aspect of the present invention there is provided an infant feed comprising the insulin formulation.

According to another aspect of the present invention there is provided a method of preventing necrotizing enterocolitis/colitis/enterocolitis in a preterm infant comprising administering to the preterm infant the infant feed.

According to another aspect of the present invention there is provided a method of reducing the prevalence and severity of necrotizing enterocolitis/colitis/enterocolitis in a preterm infant comprising administering to the preterm infant the infant feed.

According to another aspect of the present invention there is provided a method of reducing the prevalence of late-onset sepsis in a preterm infant comprising administering to the preterm infant the infant feed.

According to another aspect of the present invention there is provided a method of reducing inflammation in the gastrointestinal in a preterm infant comprising administering to the preterm infant the infant feed.

According to another aspect of the present invention there is provided a method of reducing the prevalence and severity of adverse events, life-threatening events and fatal complications in a preterm infant comprising administering to the preterm infant the infant feed.

According to another aspect of the present invention there is provided a method of reducing permeability of the GI tract in a preterm infant comprising administering to the preterm infant the infant feed and measuring a lactose/lactulose ratio.

According to another aspect of the present invention there is provided a method of increasing the rapid maturation of the gut microbiota in a preterm infant comprising administering to the preterm infant the infant feed and measuring a reduction in Proteobacteria and an increase in Firmicutes and Clostridiaceae.

According to embodiments of the present invention the infant feed includes 0.01-4 IU/ml.

According to another aspect of the present invention there is provided a method of preventing late onset sepsis in a preterm infant comprising administering to the preterm infant the infant feed.

According to another aspect of the present invention there is provided a method of reducing a discharge time from primary care of a preterm infant comprising administering to the preterm infant the infant feed disclosed herein.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE SEVERAL VIEWS OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF SPECIFIC EMBODIMENTS OF THE INVENTION

The present invention is of an insulin formulation which can be used in an infant feed. Specifically, the present invention can be used to prevent or reduce severity of pre-term infant disorders such as late onset sepsis or necrotizing enterocolitis/colitis/enterocolitis.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Insulin-containing infant feeds are known in the art and have been suggested for treatment of malabsorption in preterm infants.

While conducting experiments with various insulin formulations intended for use in infant feeds such as maternal milk or formulas, the present inventors have observed that when solubilized in infant feed, insulin exhibits the tendency to polymerize and agglomerate thus reducing the availability of insulin in the resultant feed formula. While vigorous mixing of the infant feed can partially resolve this problem, the present inventors postulated that this is a less than optimal solution and set out to improve insulin solubility in infant feed.

Thus, according to one aspect of the present invention there is provided and insulin formulation that is readily dissolvable in an infant feed (e.g., maternal milk or formula) and exhibits stability (structural and functional) in the feed without agglomeration for extended periods of time.

The present preparation includes insulin (e.g., human recombinant), a carbohydrate (e.g., oligosaccharide such as maltodextrin) and sodium chloride at a ratio of 1:A:B (w:w:w respectively), wherein ranges of A and B are 1000-100,000 and 10-50, respectively. One gram of the insulin formulation can include 2-40 IU. The insulin formulation can further include cyclodextrin at a ratio of 10-1000 with respect to the insulin. Carbohydrates such as, for example, monosaccharides (e.g. glucose), disaccharides (e.g. lactose, maltose), oligosaccharides (dextrins (e.g. Maltodextrin), cyclodextrins (e.g. Hydroxypropyl-beta-cyclodextrin (HPbCD) and polysaccharides are used as stabilizers, fillers and cryoprotectants. Buffering agents (e.g. sodium or potassium phosphate salts) can also be added to the composition.

The formulation can be combined with an oil-in-water nanoemulsion having nanodroplets that include the Docosahexaenoic acid (DHA) and coenzyme Q10.

The formulation can be in powder form and when reconstituted in deionized water or 0.9% sodium chloride solution at concentration of 0.03 g/ml can exhibit a pH of 6.0-7.6.

Figure 8:
FIG. 8 is a scanning electron micrograph showing the amorphous structure of formulations I-IV of the present invention.

The present inventors have discovered that pretreatment of insulin at pH 6.9-8.0, compounding with a carbohydrate at pH 6.7-7.6 and lyophilization, results in an amorphous insulin powder (FIG. 8) that is freely soluble in human breast milk and thus overcomes the aforementioned limitations of prior art insulin formulations.

Figure 9:
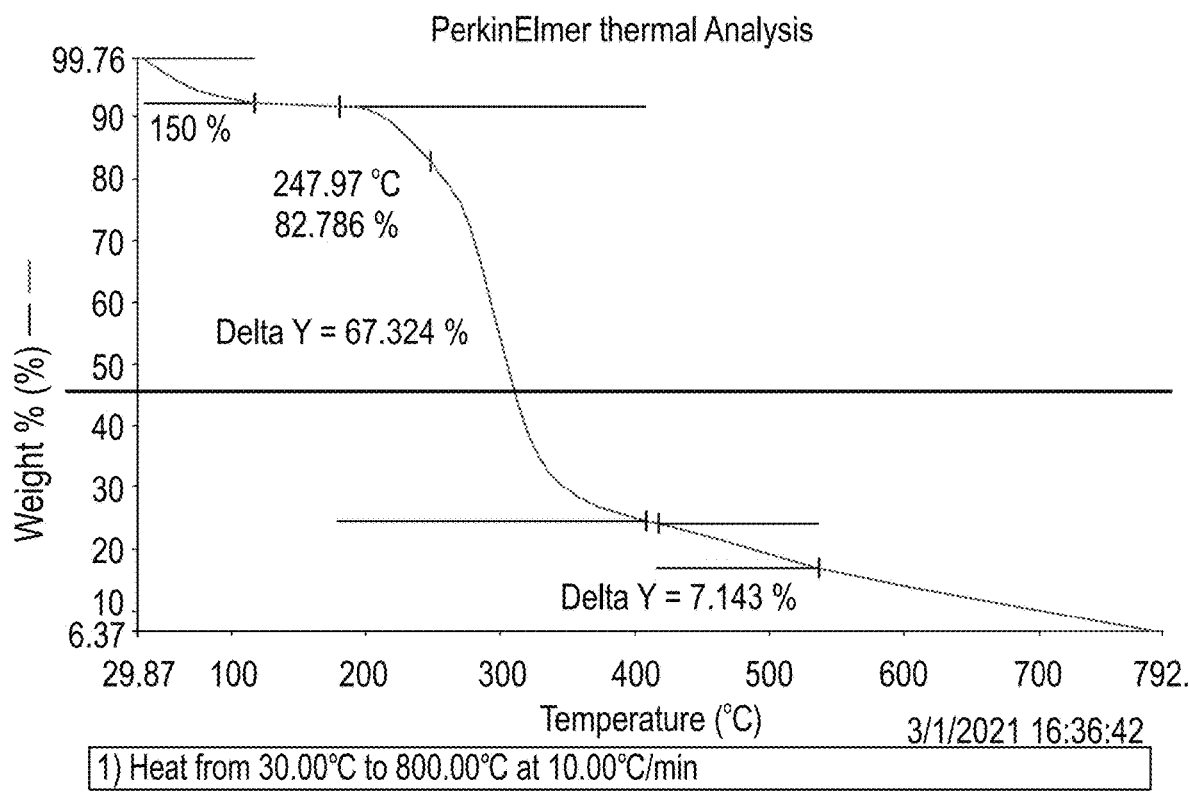
FIGS. 9-10 are graphs showing thermogravimetric analysis (TGA) and differential scanning calorimetry (DSC) of formulations I-IV of the present invention.
Figure 10:
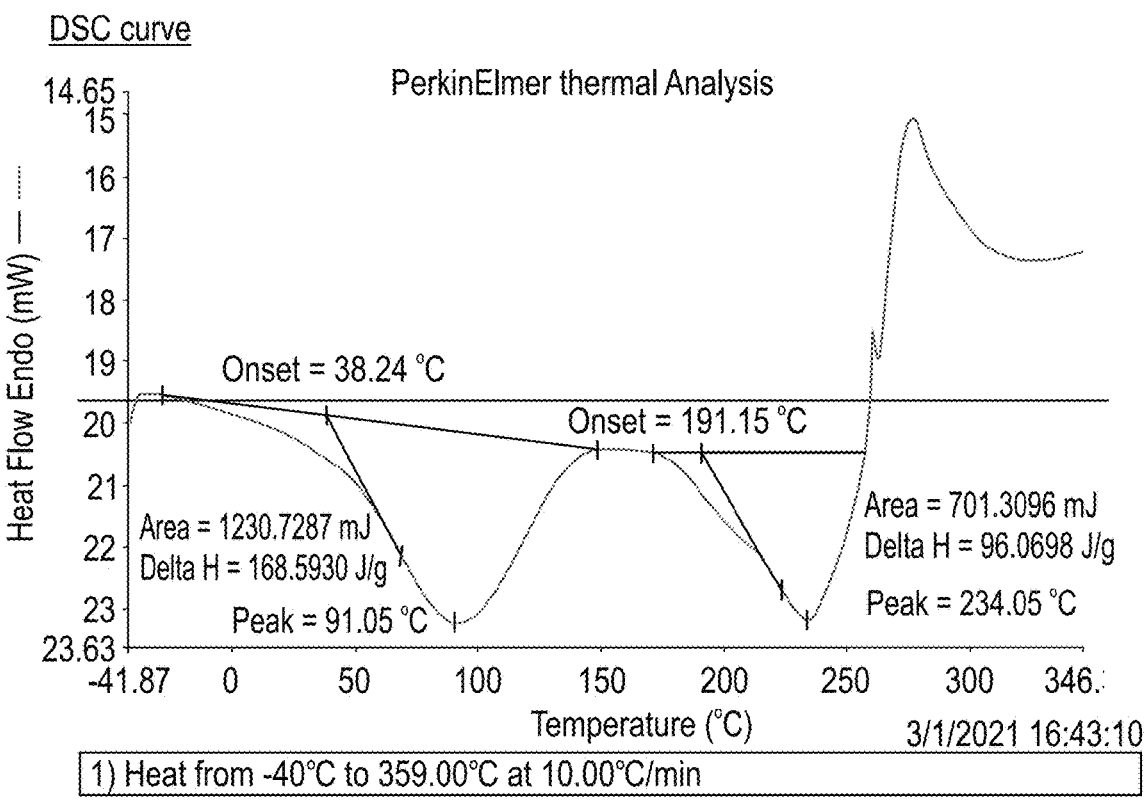
Figure 11:
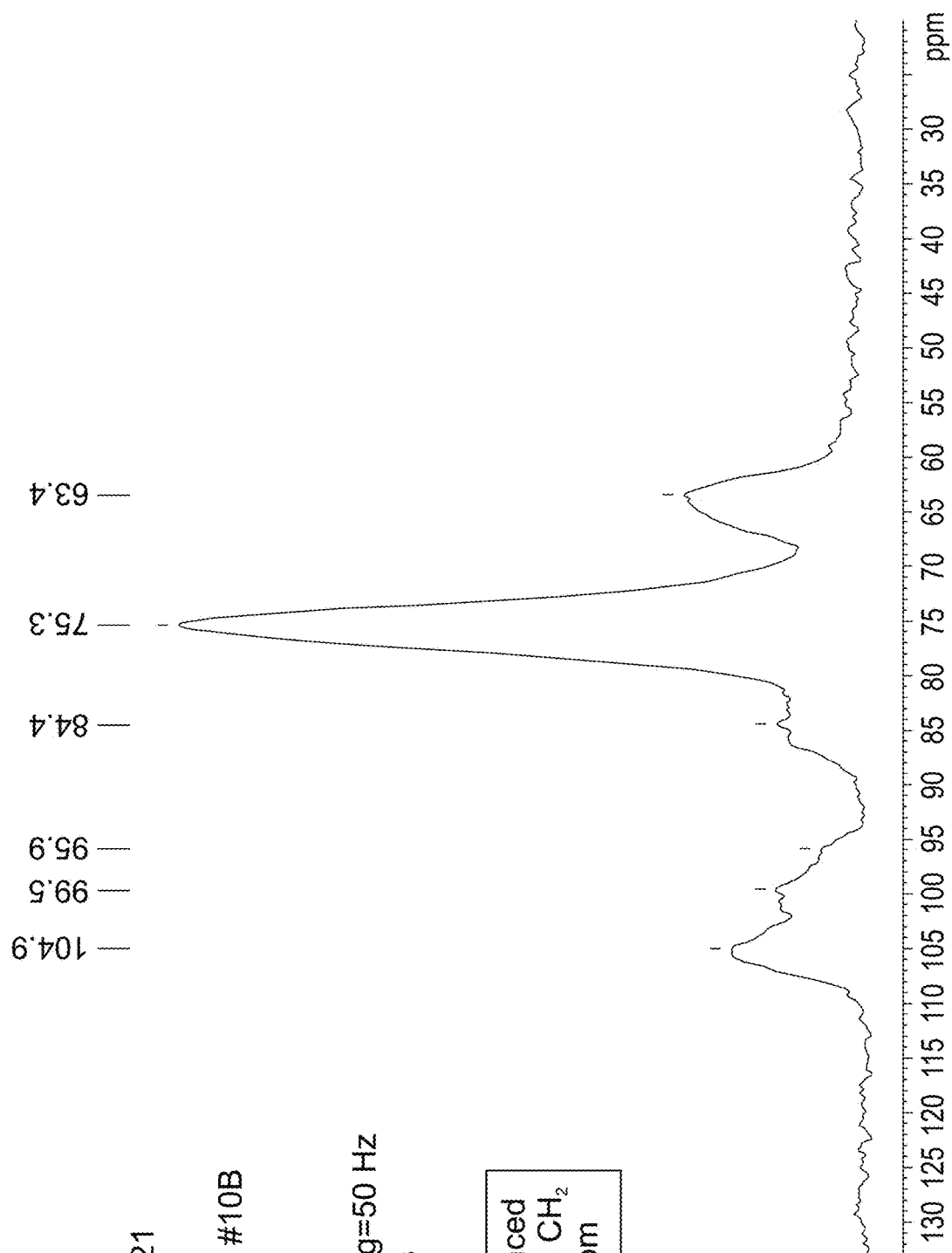
FIG. 11 is a solid-state NMR spectrum of formulation I-IV of the present invention.

The present insulin formulation is an amorphous powder in which insulin is incorporated into an amorphous structure mainly composed of a filler (e.g. maltodextrin). The water content of the preparation can be 6.5% or lower, the osmolarity is about 110-120 mosm/kg when reconstituted in deionized water at concentration of 0.1 g/ml and the pH is 6.0-7.6 when reconstituted in deionized water or 0.9% sodium chloride solution at concentration of 0.03 g/ml. Typical thermogram curves, obtained by thermogravimetric analysis (TGA) and Differential scanning calorimetry (DSC), are shown in FIGS. 9-10. Solid-state NMR spectrum of a formulation of the present, invention is provided in FIG. 11.

As is mentioned herein, the present insulin formulation can be added as a powder (or liquid) to an infant feed such as, for example, human milk. The human milk be mother breast milk or donor breast milk fresh and homogenized.

When in powder form, the present insulin formulation can be reconstituted in an infant feed to a final insulin concentration of 0.1-8 IU/ml.

The present formulation can be packaged as a powder and stored for extended time periods (days/months).

The package can be, for example, a glass vial or an aluminum sachet filled with a dry form of the present formulation. The pack can include 0.1-1.0 grams of a powder form of the formulation with each gram including 0.2-40 IU insulin. The headspace of the packaging unit can be air or inert gas (e.g. nitrogen).

The package can provide a moisture and/or oxygen barrier with a moisture vapor transmission rate (MVTR) of less than about 0.1 g/m$^2$/24 h and an oxygen transmission rate (OTR) of less than about 0.1 cm$^3$/m$^2$/24 h.

When packaged as disclosed herein, the present formulation is highly stable and can be stored for prolonged periods with insulin activity decreasing by no more than about 1-10%, when stored at between about 2° C. to about 8° C. for up to 24 months. Additionally, the water content of the packaged formulation is typically no more than about 4.5-6.5% by weight when stored at between about 2° C. to about 8° C. for 24 months.

The insulin formulation can be reconstituted in deionized water or 0.9% sodium chloride solution and the resulting solution can be added to an infant feed (Mother's Own Milk, Donor Breast Milk, Formula etc.) to provide the concentration of insulin described above for the powdered formulation.

As is described herein and demonstrated in the Examples section, the present insulin formulation and feed containing same can be used to accelerate wean-off of pre-term infants from parenteral nutrition and to substantially reduce adverse events overall, as well as specific conditions of interest including necrotizing colitis (NEC) and late onset sepsis (LOS).

Thus, according to another aspect of the present invention there is provided a method of preventing or reducing the risk and severity of, LOS in a subject in need such as a preterm infant. The method is effected by administering a therapeutically effective amount of the infant feed mixed with the drug of the present invention to the subject in need. Such administration can be oral or through a feeding tube.

Thus, according to yet another aspect of the present invention there is provided a method of preventing or reducing the risk and severity of, NEC in a subject in need such as a preterm infant. The method is effected by administering a therapeutically effective amount of the infant feed mixed with the drug of the present invention to the subject in need. Such administration can be oral or through a feeding tube.

The term "therapeutically effective amount" denotes a dose of an active ingredient or a feed comprising the active ingredient that will provide the therapeutic effect for which the active ingredient is indicated.

As used herein the phrase "subject in need thereof" refers to a human infant. The human infant can be at any age (e.g., a term or preterm infant) or of any gender. The subject in need can be a preterm infant born at a gestational age of 24 to 37 weeks or a low-birth-weight full term infant or an Intrauterine growth restriction (IUGR) infant or Small for Gestational Age infant.

A typical dose regimen established by the present inventors can be administered via continuous enteral administration or bolus intake using 0.1-1 gm of powder mixed into 1-3 ml of an infant feed divided into 1-12 oral administrations a day for example.

As is described in the Examples section that follows, the present regimen resulted in less NEC cases in the 0.3 IU/kg/day dose group compared to placebo; Necrotizing enterocolitis (Bell stage 2 or 3) occurred in 7 infants (6%) in the low-dose group, 4 infants (5%) in the high-dose group, and 10 infants (10%) in the placebo group. When observing the most fragile population (26-28 weeks gestational age strata) the difference is even more pronounced—4.3% of subjects in treatment group had NEC vs. 19.6% in the placebo group. There was a meaningful difference between groups in the percentage of infants experiencing infections (including sepsis and other infections). When observing the entire study population, the general incidence was 30% in the 0.06 IU/kg/day dose group, 34.7% in the 0.3 IU/kg/day dose group and 42.9% in the Placebo group.

A simultaneous assessment of intestinal permeability and lactase activity by sugar absorption test (SAT) performed in another study using the present regimen showed a trend towards lower intestinal permeability (indicating rapid maturation of the GI) and higher lactase activity in the treatment groups.

The efficacy of the present study is also demonstrated by the time to discharge (to home or secondary site) as is demonstrated by the results shown in Example 4. As is shown therein, a reduction of time to discharge from primary care of a preterm infant is by at least 5% as compared to an untreated preterm infant (control). This translates to discharge that is at least 5 days earlier than that expected.

Another study was performed aimed to assess the efficacy of 2 doses of enteral insulin administration compared to placebo with respect to early differences in intestinal microbiota. This study showed significant differences in GI microbiota between the treatment groups and placebo. At the end of treatment, high insulin dose showed less microbial diversity than placebo (p=0.0192). Insulin increases Firmicutes phylum and decreases Proteobacteria phylum. Enteral insulin administration had a reduction in Proteobacteria and an increase in Firmicutes and Clostridiaceae. These results indicate that the present formulation and regimen facilitate rapid maturation of gut microbiota. Decrease of Proteobacteria and increase of Firmicutes obtained in this study are the changes observed previously in low risk infants for NEC.

As used herein the term "about" refers to ±10%.

Additional objects, advantages, and novel features of the present invention will become apparent to one ordinarily skilled in the art upon examination of the following examples, which are not intended to be limiting.

EXAMPLES

Reference is now made to the following examples, which together with the above descriptions, illustrate the invention in a non-limiting fashion.

Example 1

Insulin and Infant Feed Formulations

Insulin formulations were prepared and tested (in an infant feed) for effectiveness in treating preterm infants.

Formulation I

Insulin as active ingredient, sodium chloride as solubilizing agent and oligosaccharide as filler and stabilizer (e.g. Maltodextrin). The finished product is a lyophilized powder packed in glass vials. Strength of the reconstituted solution is regulated by the diluent volume.

TABLE 1

| Ingredient | Content per unit dose (vial) |
|---|---|
| Recombinant Human Insulin (rh-Insulin) | 0.04-0.05 mg (1-1.5 IU) |
| Maltodextrin | 100-500 mg |
| Sodium Chloride | 1.0-2.0 mg |

Materials and Methods

A solution of rh-Insulin, 24.5 IU/ml, was prepared as follows: 13 mg Insulin were solubilized in 1 ml 0.1N hydrochloric acid, diluted up to 15 ml with water and the pH was adjusted to 7.6 with 0.1N sodium hydroxide.

Formulation Compounding:

Forty grams of maltodextrin were dissolved in 100 ml water and pH of the obtained solution was adjusted to 7.2. 2 ml of 6% sodium chloride solution and 4 ml of Insulin solution were added to the formulation mixture, the pH was adjusted to 7.0.

The resulting bulk was filtered through 0.22 um PES membrane, filled into the glass vials (filling volume 1.7 ml) and lyophilized.

Each vial with lyophilized powder contained 1.25 IU rh-Insulin, 510 mg maltodextrin and 1.5 mg sodium chloride.

Formulation II

Insulin as active ingredient, cyclodextrin as encapsulating agent (e.g. Hydroxypropyl Beta-Cyclodextrin), sodium chloride as solubilizing agent and oligosaccharide as filler and stabilizer (e.g. Maltodextrin). The finished product is a lyophilized powder packed in glass vials. Strength of the reconstituted solution is regulated by the diluent volume.

TABLE 2

| Ingredient | Content per unit dose (vial) |
|---|---|
| Recombinant Human Insulin (rh-Insulin) | 0.04-0.05 mg (1-1.5 IU) |
| Hydroxypropyl Beta-Cyclodextrin | 2.0 mg |
| Maltodextrin | 100 mg |
| Sodium Chloride | 1.0 mg |

Materials and Methods

A solution of rh-Insulin, 62 IU/ml, was prepared as follows: 85.6 mg Insulin were solubilized in 5 ml 0.1N hydrochloric acid, diluted with 30 ml water and the pH was adjusted to 7.2 with 0.1N sodium hydroxide.

Formulation Compounding:

Two hundred grams of maltodextrin were dissolved in 600 g water and pH of the obtained solution was adjusted to 7.3. 2 g of sodium chloride, pre-dissolved in 60 ml water, and Insulin solution were added to the formulation mixture, the pH was adjusted to 7.0 and additional portion of water was added to complete the bulk volume to 1 L.

The resulting bulk was filtered through 0.22 um PES membrane, filled into the glass vials (filling volume 0.5 ml) and lyophilized.

Each vial with lyophilized powder contained 1.2 IU rh-Insulin, 100 mg maltodextrin and 1.0 mg sodium chloride.

Formulation III

A solution of rh-Insulin, 243 IU/ml, was prepared as follows: 84.4 mg Insulin were solubilized in 1 ml 0.1N hydrochloric acid, diluted up to 10 ml with water and the pH was adjusted to 8.1 with 0.1N sodium hydroxide.

Formulation Compounding:

Thirty grams of maltodextrin were dissolved in 60 ml water and pH of the obtained solution was adjusted to 7.1. 2.7 ml of 7.5% sodium chloride solution and 1 ml of Insulin solution were added to the formulation mixture, the pH was adjusted to 7.3 and additional portion of water was added to complete the bulk weight to 100 g.

The resulting bulk was filtered through 0.22 um PES membrane, filled into the glass vials (filling volume 0.5 ml) and lyophilized.

Each vial with lyophilized powder contained 1.4 IU rh-Insulin, 172 mg maltodextrin and 1.2 mg sodium chloride.

Formulation IV

This example describes the formulation produced at commercial scale 9 kg of the liquid bulk (0.9 kg of the lyophilized powder). Insulin as active ingredient, sodium chloride as solubilizing agent and oligosaccharide as filler and stabilizer (e.g. Maltodextrin). The finished product is a lyophilized powder packed in glass vials. Strength of the reconstituted solution is regulated by the diluent volume.

TABLE 3

| Ingredient | Content per unit dose (vial) |
|---|---|
| Recombinant Human Insulin (rh-Insulin) | 0.035 mg (1 IU) |
| Maltodextrin | 99 mg |
| Sodium Chloride | 1 mg |
| Total weight | 100 mg |

Materials and Methods

A solution of rh-Insulin, 33 IU/ml, was prepared as follows: 0.39 g Insulin were solubilized in 20 g 0.1N hydrochloric acid, diluted with 300 g water for injection and then neutralized with 20 g of 0.1N sodium hydroxide. The pH was adjusted to 7.2 with 0.1N sodium hydroxide.

Formulation Compounding:

856 grams of maltodextrin and 8.6 gram of sodium chloride were dissolved in 6854-gram water and pH of the obtained solution was adjusted to 7.2. The insulin solution was added to the compounding mixture, the weight of the resulting formulation was adjusted up to 9.0 kg and the pH was adjusted to 7.0.

The resulting bulk was filtered through 0.22 um PES membrane, filled into the glass vials (filling volume 1 g) and lyophilized.

Each vial with lyophilized powder contained 1U rh-Insulin, 99 mg maltodextrin and 1 mg sodium chloride.

Analytical characteristics of the obtained dry powder are: content of Insulin (insulin+A21 desamido insulin) is 1.13 IU/vial, content of A21 desamido insulin is 0.5% (by area percent), content of other total related substances is 0.1% (by area percent), relative standard deviation of insulin content per vial (uniformity) is 0.9%, water content is 0.8%, pH is 6.7, reconstitution time of the powder in water is below 5 minutes.

Formulation V

This formulation was produced by forming a DHA and Coenzyme Q10 emulsion using a solvent displacement method, adding rh-Insulin and cryoprotectant (e.g. dextrins, cyclodextrins), filtrating and lyophilizing.

TABLE 4

| Ingredient | Content per unit dose (vial) |
| --- | --- |
| Recombinant Human Insulin (rh-Insulin) | 0.04 mg (1.2 IU) |
| Cis-4,7,10,13,16,19-Docosahexaenoic acid (DHA) | 2.5 mg |
| Coenzyme Q10 (CoQ10) | 1.1 mg |
| Tyloxapol | 0.5 mg |
| Lipoid E 80 | 0.5 mg |
| Polyvinyl alcohol (PVA) | 0.5 mg |
| Maltodextrin | 33 mg |
| Sodium hydroxide* | — |
| Hydrochloric acid* | — |

*Sodium hydroxide or hydrochloric acid are used for adjusting the pH value and not included in the sum.

Materials and Methods

A solution of rh-Insulin, 40 IU/ml, was prepared as follows: 27.5 mg Insulin were solubilized in 2 ml 0.1N hydrochloric acid, diluted with 18 ml water and the pH was adjusted to 7.2 with 0.1N sodium hydroxide.

An oil in water nanoemulsion (average droplet size 120 nm) was prepared as follows: 690 mg of Coenzyme Q10, 1533 mg of DHA ethyl ester, 300 mg Tyloxapol and 300 mg Lipoid E80 were dissolved in 56 ml Ethanol. The mixture was added dropwise through 21 G needle to 300 ml of 0.1% PVA aqueous solution continuously mixed at 350 RPM at room temperature. Resulting emulsion was mixed for additional 10 minutes, diluted with 0.1% PVA solution and the organic solvents were removed via tangential flow filtration using Hydrosart, MWCO 30,000 membrane.

Ten grams of maltodextrin were dissolved in 160 ml of the obtained emulsion and then mixed with Insulin solution. The volume of the final bulk was completed to 300 ml and the pH was adjusted to 6.9. The emulsion was filtered through 0.22 um PES membrane, filled into glass vials (filling volume 1 ml/vial) and lyophilized. Each vial contains 1.2 IU rh-Insulin, 2.5 mg DHA and 1.1 mg Coenzyme Q10. The average size of the droplet particles in the reconstituted powder is 295 nm.

Formulation VI

Formulation steps are identical to those of formulation V.

TABLE 5

| Ingredient | Content per unit dose (vial) |
| --- | --- |
| Recombinant Human Insulin (rh-Insulin) | 0.04 mg (1.2 IU) |
| Cis-4,7,10,13,16,19-Docosahexaenoic acid (DHA) | 2.3 mg |
| Coenzyme Q10 (CoQ10) | 1.1 mg |
| Tyloxapol | 0.5 mg |

TABLE 5-continued

| Ingredient | Content per unit dose (vial) |
| --- | --- |
| Lipoid E 80 | 0.5 mg |
| Polyvinyl alcohol (PVA) | 0.5 mg |
| Hydroxypropyl Beta Cyclodextrin | 30 mg |
| Sodium hydroxide* | — |
| Hydrochloric acid* | — |

*Sodium hydroxide or hydrochloric acid are used for adjusting the pH value and not included in the sum.

Materials and Methods

A solution of rh-Insulin, 40 IU/ml, was prepared as follows: 27.2 mg Insulin were solubilized in 2 ml 0.1N hydrochloric acid, diluted with 18 ml water and the pH was adjusted to 7.2 with 0.1N sodium hydroxide.

An oil in water nanoemulsion (average droplet size 120 nm) was prepared as described for formulation IV.

Ten grams of Hydroxypropyl Beta Cyclodextrin were dissolved in 160 ml of the obtained emulsion and then mixed with Insulin solution. The volume of the final bulk was completed to 327 ml and the pH was adjusted to 6.9. The emulsion was filtered through 0.22 um PES membrane, filled into glass vials (filling volume 1 ml/vial) and lyophilized. Each vial contains 1.2 IU rh-Insulin, 2.5 mg DHA and 1.1 mg Coenzyme Q10. The average size of the droplet particles in the reconstituted powder is 143 nm.

Example 2

Testing of Formulations I-IV

Figure 1:
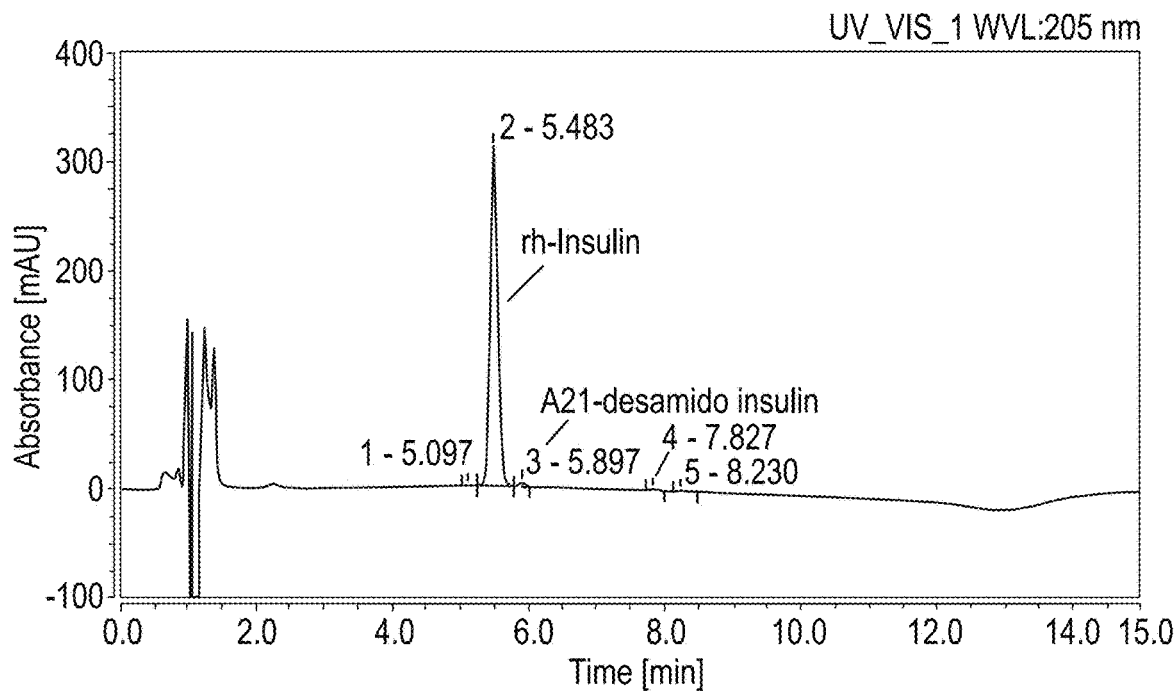
FIG. 1 is a typical chromatogram of formulations I-IV of the present invention.

The content of rh-Insulin was determined by reverse-phase high performance liquid chromatography method on Hypersil Gold-C18 column (3×50 mm, 3 μm) and gradient elution with a mobile phase composed of aqueous and organic phases (acetonitrile) acidified with 0.1% trifluoroacetic acid (TFA). Flow rate—0.3 ml/min, UV detection at 205 nm. A typical chromatogram of formulations I-IV is shown in FIG. 1.

Testing of Formulations V-VI

Figure 2:
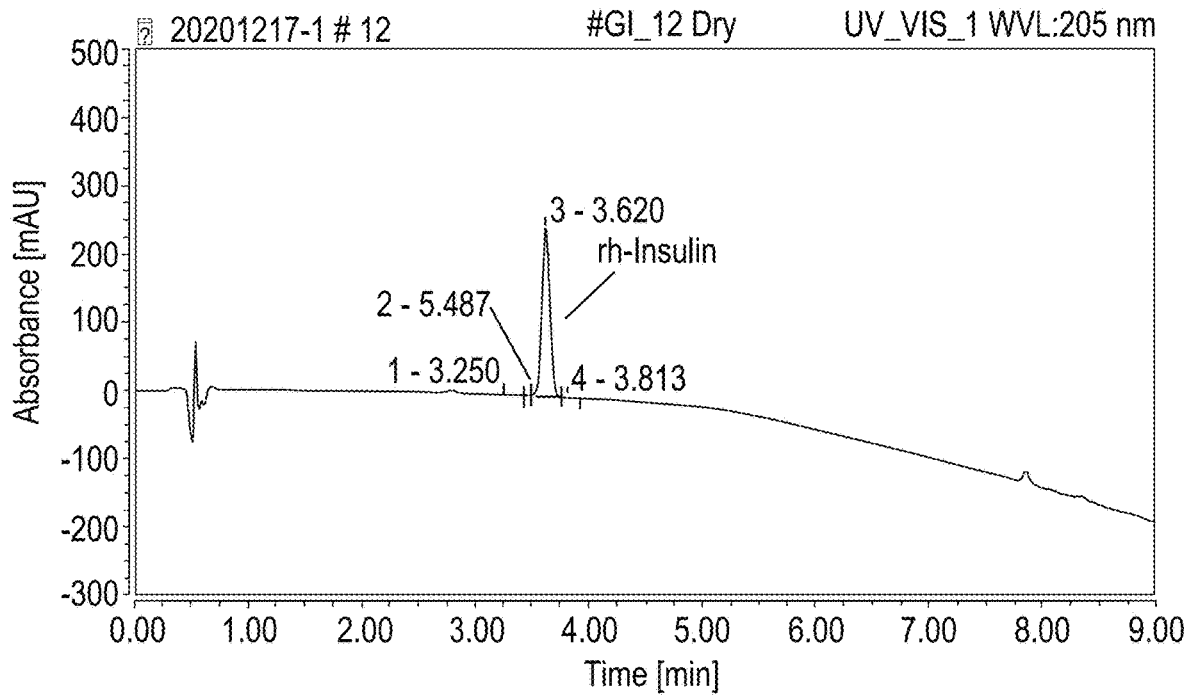
FIG. 2 is a typical chromatogram of formulations V-VI of the present invention.
Figure 3:
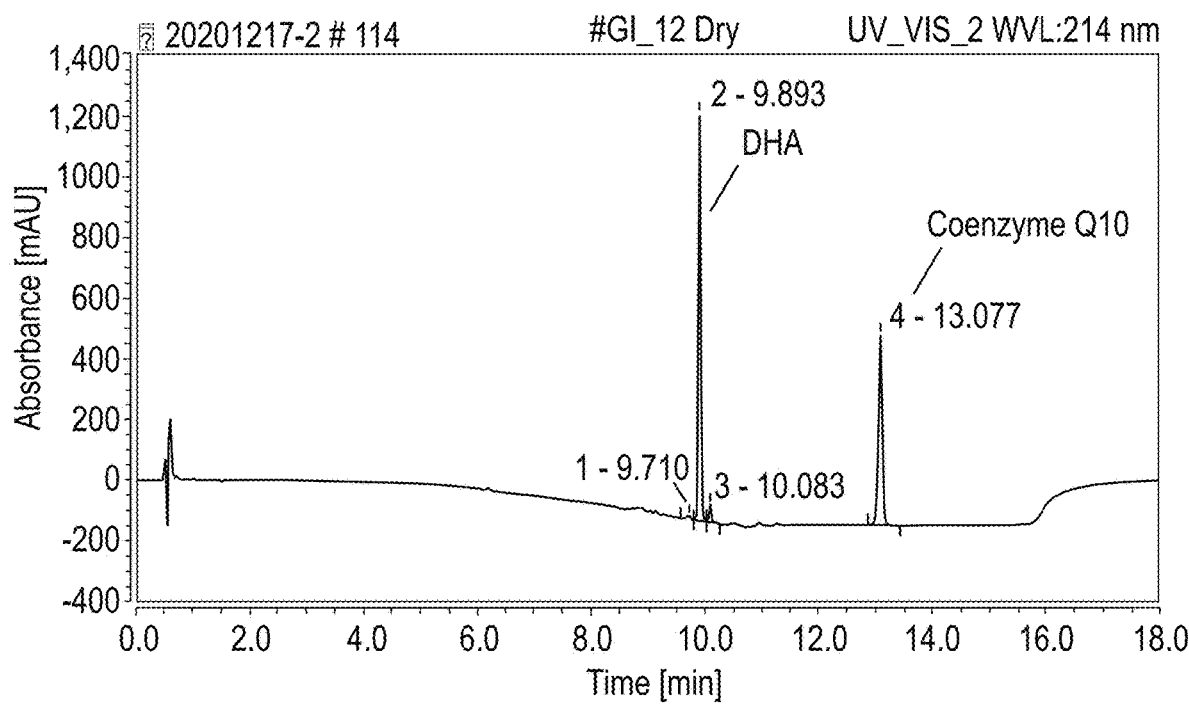
FIG. 3 is a typical chromatogram of DHA and Coenzyme Q10 in formulations IV-V of the present invention.

The content of rh-Insulin, DHA and Coenzyme Q10 was determined by reverse-phase high performance liquid chromatography method on Hypersil Gold-C18 column (3×50 mm, 3 μm) and gradient elution with a mobile phase composed of aqueous and organic phases (mixture of acetonitrile:methanol:2-propanol 75:15:10) acidified with 0.1% trifluoroacetic acid (TFA). Flow rate—0.6 ml/min, UV detection at 205 nm for Insulin and 214 nm for DHA and Coenzyme Q10. A typical chromatogram of formulations V-VI is shown in FIG. 2. A typical chromatogram of DHA and Coenzyme Q10 determination in formulations V-VI is shown in FIG. 3.

Example 3

Infant Feed Solubility

A study was designed to assess solubility of the present formulation at a pH range of human breast milk. Three dry samples, containing maltodextrin, sodium chloride and insulin (1 IU) were prepared as follows.

Sample 1 is a crystalline, thermally dried powder, prepared by spraying a solution of maltodextrin, sodium chloride and insulin onto solid maltodextrin particles and subsequent drying at 35° C. Dried powder was mixed 1:3 with maltodextrin, the final pH was 6.3.

Sample 2 is one variant of the present formulation, presented as an amorphous powder, at pH 7.0, prepared as described in Example 1, Formulations I-III.

Sample 3 is a physical mixture of dry ingredients (maltodextrin, sodium chloride and insulin), dry blended without any pretreatment.

A certain amount of each formulation (equivalent to 1 IU of insulin) was reconstituted in 1.8 ml of 0.1M phosphate buffer at pH 6.3, 6.7 and 7.2 and visually examined.

The results show that Sample 2 (the present formulation) dissolves freely in the wide pH range of breast milk (6.3-7.2), resulting in a clear solution comparable to the reference buffer. Sample 1 (thermally dried formulation) and Sample 3 (physical blend of dry ingredients, no pretreatment) were partially soluble in the tested pH range, resulting in a cloudy solution.

The dissolution profile of the test samples was evaluated using HPLC in the following media:

0.01 N. HCl, double deionized water and 0.1 M phosphate buffer at pH 6.3 and 7.4.

For each sample, the percentage of dissolution in water and phosphate buffer was calculated relative to the amount of insulin determined in 0.01 N. HCl. The dissolution results obtained (Table 6 below) indicate that the present composition is highly soluble in the pH range of infant formula.

TABLE 6

| | % Dissolution of Insulin | | |
|---|---|---|---|
| Dissolution medium | Sample 1 (thermal drying) | Sample 2- present formulation (freeze drying) | Sample 3 (physical blend of dry ingredients, no pre-treatment) |
| 0.01 N HCl | 100.0% | 100.0% | 100% |
| Double deionized water | 84.0% | 93.1% | 68.1% |
| 0.1 M Phosphate buffer, pH 6.3 | 78.9% | 93.3% | 81.8% |
| 0.1 M Phosphate buffer, pH 7.4 | 84.3% | 93.6% | 95.0% |

In addition, samples 1 and 2 were reconstituted in cow's milk (pH 6.89, fat content 3%). The results were consistent with observations of the buffer recovery test. Sample 1 is partially reconstituted in milk, resulting in visible clots that can adhere or block the passage of the reconstituted drug through the nasogastric tube. Sample 2 is completely reconstituted in milk, resulting in a homogeneous mixture.

Example 4

Pre-Term Infant Study—Efficacy

A study was designed to assess the efficacy and safety of an enteral rh-insulin formulation in preterm infants. Following screening procedures, eligible infants born between 26 and up to 32 weeks of pregnancy and weighing at least 500 g at birth were to be randomly assigned to 1 of the 3 treatment groups in a 1:1:1 ratio.

Treatment commenced at postnatal age of at least 6 hours through and including 120 hours post birth. The treatment period for infants who were fed solely on own mother's milk (OMM) commenced within the first 72 hours post birth.

The treatment period was defined as the first day of dosing (Day 1) for up to 28 days or until discharge from primary hospital, if prior to Day 28.

The tested formulation was administered at 0.3 IU/Kg/Day for up to 28 days. Prior to administration, the powder was reconstituted mostly in human breast milk, donor breast milk, saline or half saline.

Results

Infants were discharged to either home or to secondary site from primary hospital. When analyzing time to discharge, two analyses are presented: 1) analysis of discharge from primary recruiting hospital (separate comparisons of subjects transferring to secondary hospital and subjects discharged home); and 2) discharge to home (either from primary or secondary hospital).

Time to Discharge from Primary Hospital

Infants were discharged from primary hospital to either home or to a secondary hospital, depending mostly on region. Each infant in the ITT analysis had one destination for analysis, by that each arm and strata were compared. Both treatment arms had significantly shorter time to discharge compared to placebo, demonstrating faster time to stable well-being.

The Median number of days to discharge from hospital (to either home or secondary hospital) was lowest in the insulin formulation comprising 0.3 IU/Kg group [median=42.0 days, P=0.055], followed by the Insulin formulation comprising 0.0406 IU/Kg group [median=43.0 days, p=0.04*] compared to placebo [median=49.5 days].

Time to Discharge to a Secondary Site

Some hospitals discharge infants to secondary sites after infants stabilize and are out of immediate life threatening condition. Infants are discharged to secondary sites and several weeks later—to home. In the trial, subjects in the Insulin formulation comprising 0.3 IU/Kg group were discharged earlier than patients in the placebo group to a secondary site—as indicated by the medians and difference from placebo (Table 7 below).

TABLE 7

Number of Days to Discharge from Primary Hospital to a Secondary Site by Gestation Age - Full Analysis Set

| | | Treatment | | |
|---|---|---|---|---|
| Gestation Age Group | Statistic | Enteral rh-insulin formulation 0.06 IU/kg/day (N = 108) | Enteral rh-insulin formulation 0.3 IU/kg/day (N = 94) | Placebo (N = 98) |
| 26 - 28 weeks | n | 14 | 16 | 14 |
| | Median | 34.0 | 31.5 | 39.0 |
| | Difference from placebo | 3.5 | 5.3 | — |
| 29 - 32 weeks | n | 8 | 5 | 12 |
| | Median | 22.0 | 11.0 | 23.0 |
| | Difference from placebo | −2.3 | 9.0 | — |

Time to Discharge to Home

Another type of analysis performed assessed the time to discharge home for all infants, regardless of if the discharge was directly from primary hospital or followed a secondary site/unit. This analysis showed a similar trend for reduction in time to discharge, however showed much larger variability compared to the main analysis 'discharge from primary hospital'.

Relative to placebo, treatment with Insulin formulation comprising 0.06 IU/Kg resulted in significantly fewer days to discharge to home [median=48.0 days vs median=60.0 days in placebo, P=0.025*]. Treatment with Insulin formulation comprising 0.3 IU/Kg resulted in a median of 55.0 days to discharge to home [p=0.27 versus placebo].

When analyzing both treatment arms together, treatment groups discharge was earlier [median=52 days, p=0.046] compared to placebo [median=60 days].

Time to Wean-Off PN

A statistically significant difference in time to weaning off parenteral nutrition (PN) was observed in the group fed an insulin-supplemented feed at a concentration of 0.3 IU/kg/day compared to placebo (6 vs. 8 days, p=0.0096**).

Figure 4:
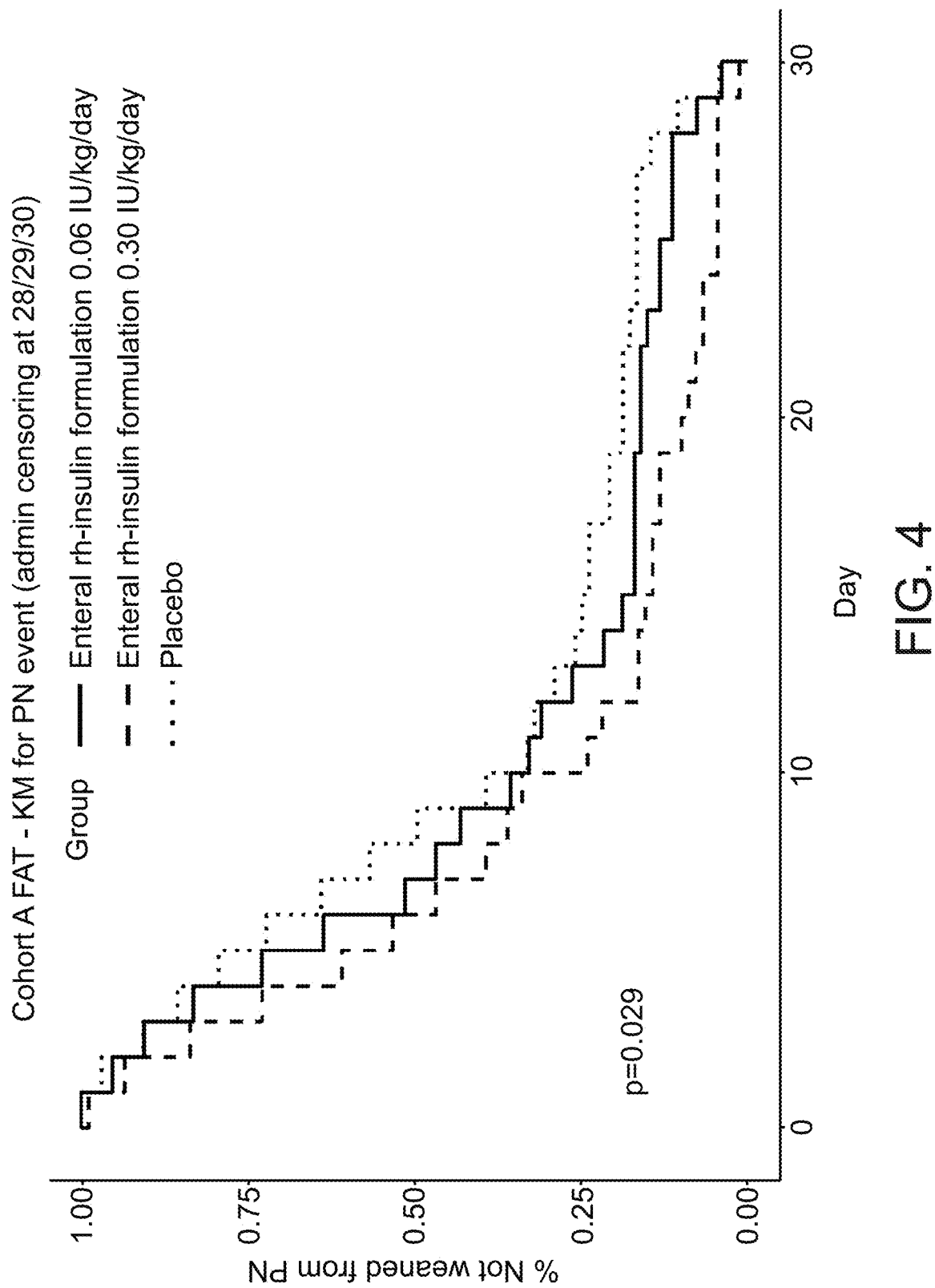
FIG. 4 illustrates the Probability of parenteral nutrition (PN) wean-off per group (Kaplan-Meier survival curve).

In assessing the time to wean-off PN by gestation age group, in the older population (29-32 weeks) time to weaning off PN was also shorter in the 0.3 IU/kg/day group (4 vs. 6 days). The results are summarized in Tables 8-10 below and graphically presented in FIG. 4 which shows the Probability of PN wean-off per group (Kaplan-Meier survival curve).

TABLE 8

Analysis Summary of Number of Days to Wean-off PN- Full Analysis Set

| Gestation Age Group | Statistics | Enteral rh-insulin formulation 0.06 IU/kg/day (N = 108) | Enteral rh-insulin formulation 0.3 IU/kg/day (N = 94) | Placebo (N = 98) |
|---|---|---|---|---|
| All | n (%) | 107 | 92 | 97 |
|  | Median | 7.0 | 6.0 | 8.0 |

TABLE 9

Analysis Summary of Number of Days to Wean-off PN- Full Analysis Set

| Gestation Age Group | Treatment Comparison | Stratified Van Elteren Test p-value |
|---|---|---|
| All | Enteral rh-insulin formulation 0.06 IU/kg/day (N = 107) vs. Placebo (N = 97) | 0.48 |
|  | Enteral rh-insulin formulation 0.3 IU/kg/day (N = 92) vs. Placebo (N = 97) | 0.0096** |

Note:
stratification factor: gestation age group (26-28 weeks, 29-32 weeks)

TABLE 10

Analysis Summary of Number of Days to Wean-off PN by Gestation Age - Full Analysis Set

| Gestation Age Group | Statistics | Enteral rh-insulin formulation 0.06 IU/kg/day (N = 108) | Enteral rh-insulin formulation 0.3 IU/kg/day (N = 94) | Placebo (N = 98) |
|---|---|---|---|---|
| 26 - 28 weeks | n | 48 | 59 | 51 |
|  | Median | 9.0 | 9.0 | 9.0 |
| 29 - 32 weeks | n | 59 | 47 | 46 |
|  | Median | 6.0 | 4.0 | 6.0 |

Another important endpoint for this study is the percentage of PN out of the total intake of the infant, as well as the gradual reduction in percentage of PN intake over time.

Figure 5:
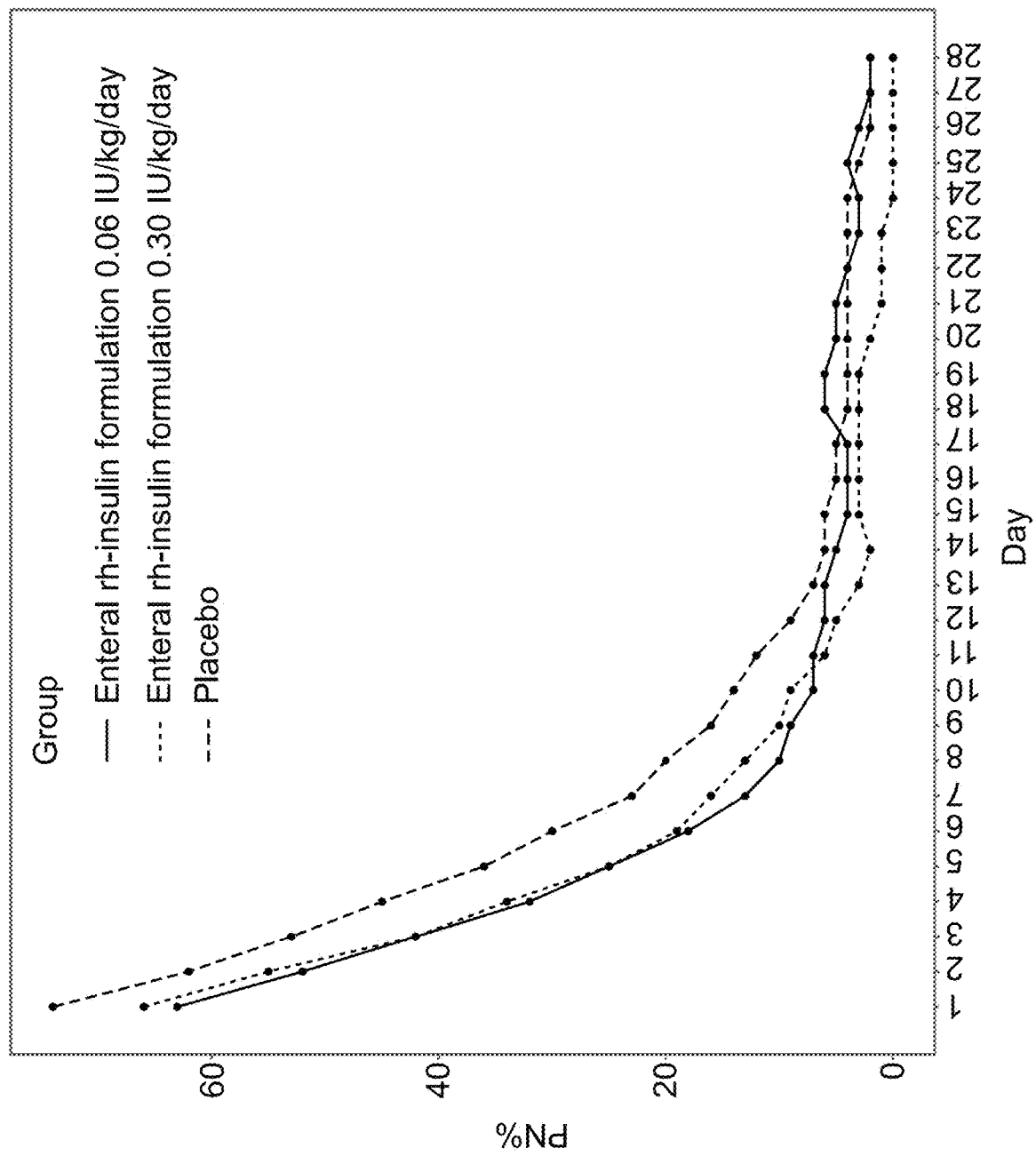
FIG. 5 illustrates the average PN intake per day per group, presenting a clear benefit of the treatment group, especially for the Enteral insulin formulation at 0.3 IU/kg/day compared to placebo (shown as the rate of PN reduction out of total intake).

FIG. 5 shows the average PN intake per day per group, presenting a clear benefit of the treatment group, especially Enteral rh-insulin formulation 0.3 IU/kg/day compared to placebo in the rate of PN reduction out of total intake.

Figure 6:
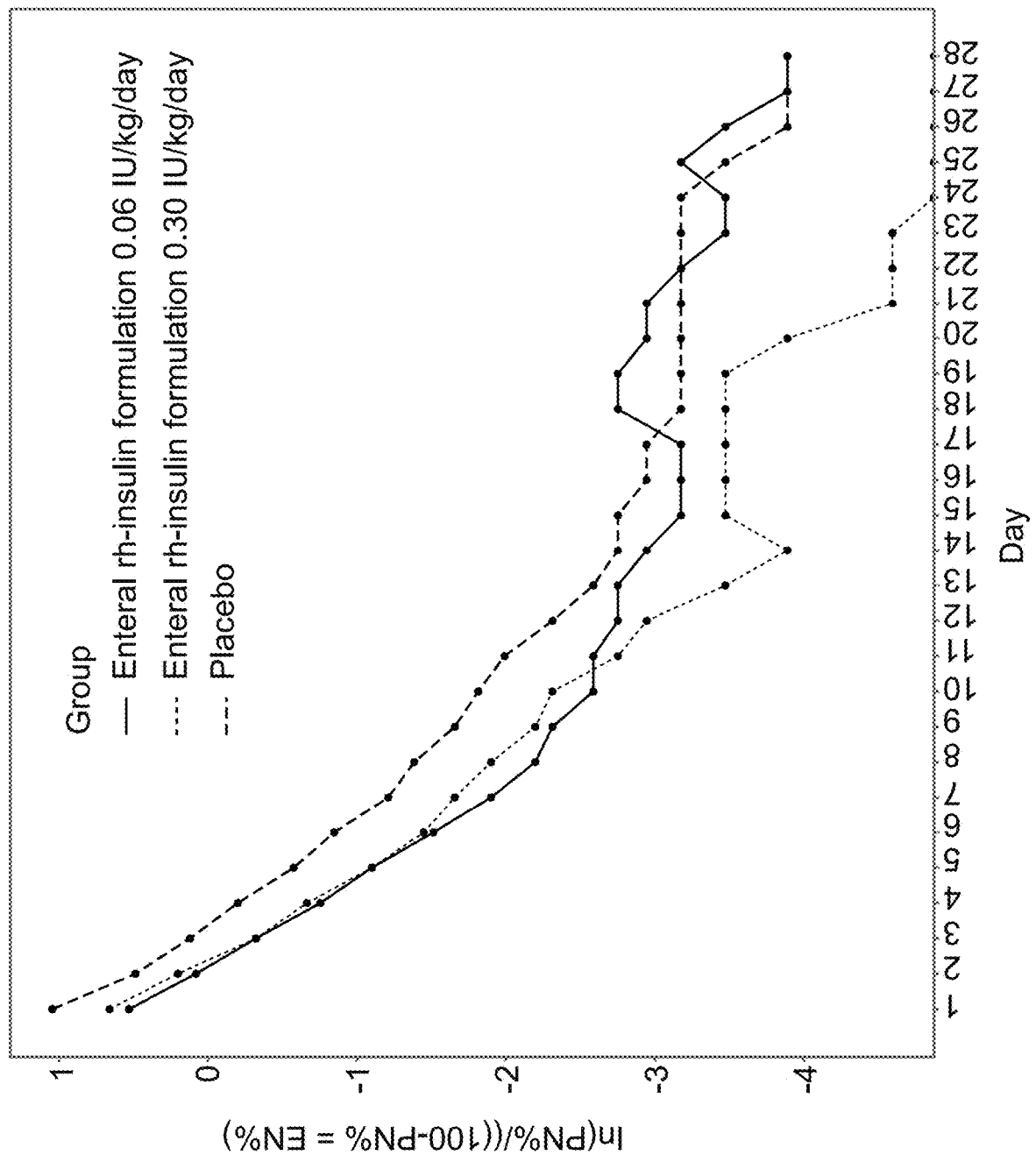
FIG. 6 illustrates the percentage of enteral nutrition out of total nutrition per group.
Figure 7:
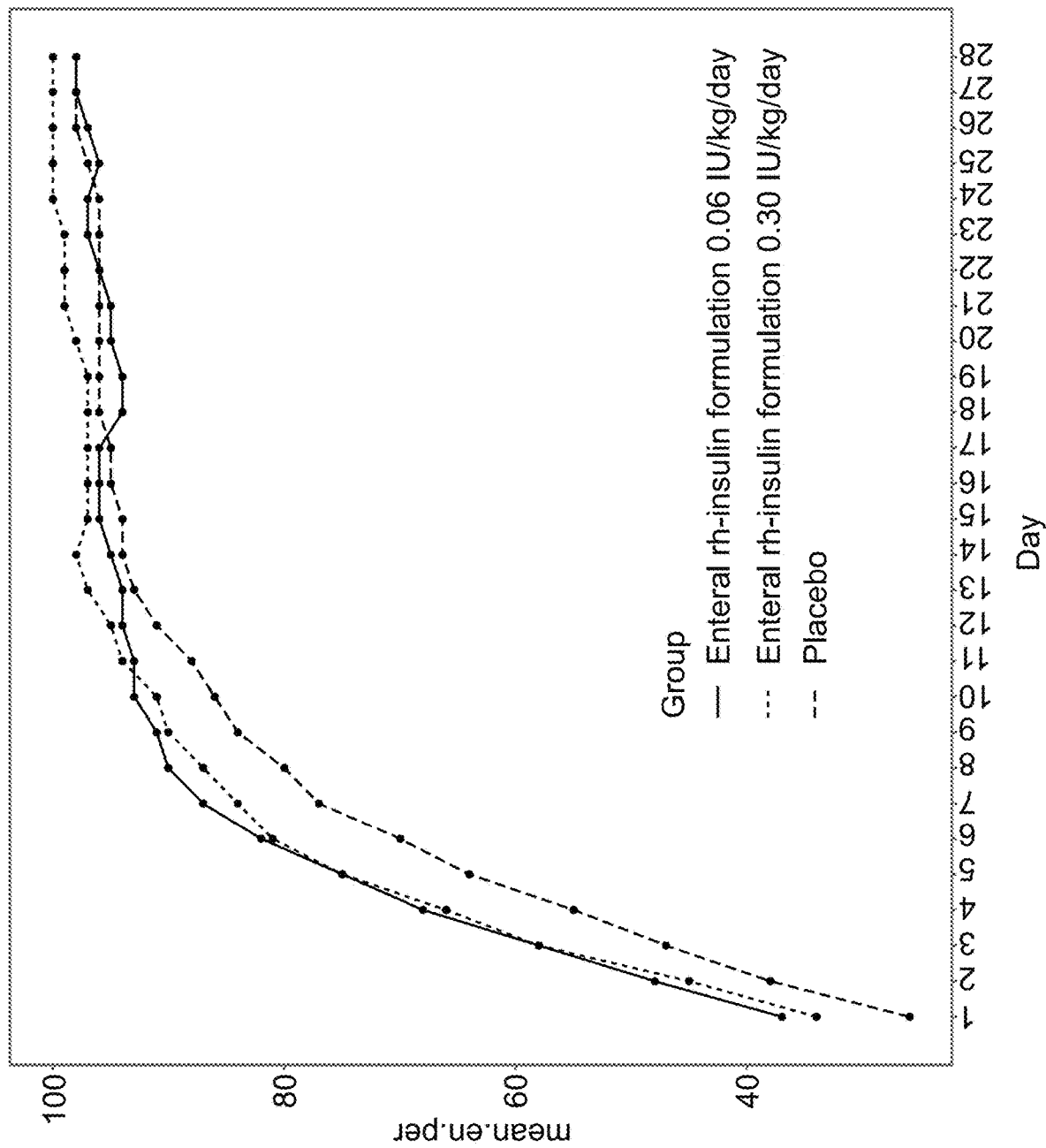
FIG. 7 illustrates the resents the trajectories per group of FIG. 6.

FIG. 6 presents the percentage of enteral nutrition out of total nutrition per group while FIG. 7 presents the Trajectories per group.

Example 5

Pre-Term Infant Study—NEC and LOS

The study population was also observed for adverse events such as necrotizing colitis (NEC) and late onset sepsis (LOS).

Necrotizing Colitis (NEC)

There was a meaningful difference between groups in the percentage of infants experiencing NEC. When observing the entire study population, general incidence was 6.3% in the 0.06 IU/kg/day dose group, 4.3% in the 0.3 IU/kg/day dose group and 10.2% in the Placebo group resulting in 60% less NEC cases in the 0.3 IU/kg/day dose group compared to placebo.

When observing the younger study population (26-28 weeks GA) where NEC is more prevalent, differences becomes even more apparent 12.2% in the 0.06 IU/kg/day dose group, 4.3% in the 0.3 IU/kg/day dose group and 19.6% in the Placebo group, resulting in nearly 80% less NEC cases in 0.3 IU/kg/day dose group compared to placebo.

A statistical analysis was performed which compared both the incidence and severity of NEC, using a non-parametric Kruskal-Wallis method, and showed a meaningful statistical difference in the 26-28 GA group (p=0.077). The results of this study are presented in Tables 11 and 12 below.

TABLE 11

NEC incidence X severity distribution per group all population

| NEC CTCAE grade | 1 | 2 | 3 | 4 | 5 | Total % |
|---|---|---|---|---|---|---|
| ENTERAL RH- INSULIN FORMULATION 0.06 IU/kg/day (N = 110) | | | | | | |
| Number of cases | 0 | 3 | 1 | 1 | 2 | 7 |
| % | 0.0% | 2.7% | 0.9% | 0.9% | 1.8% | 6.3% |
| ENTERAL RH- INSULIN FORMULATION 0.3 IU/kg/day (N = 95) | | | | | | |
| Number of cases | 0 | 0 | 2 | 1 | 1 | 4 |
| % | 0.0% | 0.0% | 2.1% | 1.1% | 1.1% | 4.3% |
| Placebo (N = 98) | | | | | | |
| Number of cases | 0 | 1 | 3 | 2 | 4 | 10 |
| % | 0.0% | 1.0% | 3.1% | 2.0% | 4.1% | 10.2% |

TABLE 12

NEC incidence X severity distribution per group (26-28 weeks GA)

| NEC CTCAE grade | 1 | 2 | 3 | 4 | 5 | Total % |
|---|---|---|---|---|---|---|
| ENTERAL RH- INSULIN FORMULATION 0.06 IU/kg/day (N = 49) | | | | | | |
| Number of cases | 0 | 3 | 0 | 1 | 2 | 6 |
| % | 0.0% | 6.1% | 0.0% | 2.0% | 4.0% | 12.2% |
| ENTERAL RH- INSULIN FORMULATION 0.3 IU/kg/day (N = 46) | | | | | | |
| Number of cases | 0 | 0 | 0 | 1 | 1 | 2 |
| % | 0.0% | 0.0% | 0.0% | 2.1% | 2.1% | 4.3% |
| Placebo (N = 51) | | | | | | |
| Number of cases | 0 | 1 | 3 | 2 | 4 | 10 |
| % | 0.0% | 1.9% | 5.8% | 3.9% | 7.8% | 19.6% |

Poor outcome composite of occurrence of one of infections, NEC and death were calculated and compared between groups and shown in Table 13 below.

TABLE 13

| Category | Enteral rh-insulin formulation 0.06 IU/kg/day (N = 110) | Enteral rh-insulin formulation 0.3 IU/kg/day (N = 95) | Placebo (N = 98) |
|---|---|---|---|
| Total subjects with infections n (%) | 33 (30.0) | 33 (34.7) | 42 (42.9) |
| Total subjects with NEC n (%) | 7 (6.4) | 4 (4.2) | 9 (9.2) |
| Total subjects experienced death n (%) | 5 (4.5) | 1 (1.1) | 4 (4.1) |
| Total subjects with any event n (%) | 38 (34.5) | 34 (35.8) | 49 (50.0) |

It was found that treatment groups had significantly lower percentage of subjects experiencing one of these adverse events of interest. Rates were 34.5% in enteral Rh insulin formulation 0.06 IU/kg/day dose group, 35.8% in the enteral Rh insulin formulation 0.3 IU/kg/day dose group and 50% in the Placebo group. When performing pairwise comparison of proportions—difference between in enteral Rh insulin formulation 0.06 IU/kg/day to Placebo p=0.034, difference between enteral Rh insulin formulation 0.3 IU/kg/day to placebo p=0.065 (see Table 14 below).

TABLE 14

Summary of analysis - pairwise comparison of proportions of safety composite

| Gestation Age Group | Comparison | Chi-squared test of independence Test p-value |
|---|---|---|
| All | ENTERAL RH-INSULIN FORMULATION 0.06 IU/kg/day (N = 110) vs. Placebo (N = 98) | 0.034* |
| | ENTERAL RH-INSULIN FORMULATION 0.3 IU/kg/day (N = 95) vs. Placebo (N = 98) | 0.065 |

Late Onset Sepsis (LOS)

There was a meaningful difference between groups in the percentage of infants experiencing infections (including sepsis and other infections). When observing the entire study population, the general incidence was 30% in the 0.06 IU/kg/day dose group, 34.7% in the 0.3 IU/kg/day dose group and 42.9% in the Placebo group.

Specifically, when measuring the rate of clinical or culture proven sepsis, treatment groups had lower rates compared to placebo. Incidence was 12% in the 0.06 IU/kg/day dose group, 11% in the 0.3 IU/kg/day dose group and 15% in the Placebo group (almost 30% reduction in late onset sepsis incidence).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A composition-of-matter comprising an amorphous insulin powder soluble in water, said amorphous insulin powder including insulin attached to dextrin particles at a gram/gram (g/g) insulin-to-dextrin ratio from 1:2500 to 1:10000, wherein 1 gram of said amorphous insulin powder includes from 10 IU to 40 IU of insulin, and further wherein when reconstituted in deionized water at a concentration of 0.03 g of amorphous insulin powder per 1 ml water, a pH of a formed solution is 6.0-7.6.

2. The composition-of-matter of claim 1, further comprising sodium chloride at a g/g sodium chloride-to-dextrin ratio from 1:100 to 1:250 and sodium chloride-to-insulin ratio from 1:20 to 1:50.

3. The composition-of-matter of claim 1, wherein said dextrin is maltodextrin.

4. The composition-of-matter of claim 1, wherein said dextrin is cyclodextrin.

5. An infant nutrition powder comprising the composition-of-matter of claim 1.

6. The composition-of-matter of claim 1, wherein said insulin is sequestered within cavities of said dextrin particles.

7. A method of preparing an amorphous insulin powder soluble in water comprising:
 (a) solubilizing insulin in hydrochloric acid to obtain solubilized insulin;
 (b) diluting said solubilized insulin with water and adjusting a pH to 6.9-8.0.
 (c) dissolving dextrin in water and adjusting pH to 7.0-7.5
 (d) adding insulin solution (b) to dextrin solution (c) to thereby sequester said insulin in cavities of said dextrin molecules;
 (e) adjusting pH of solution (d) to 6.9-8.0; and
 (f) freeze drying the solution of (e) to obtain the amorphous insulin powder.

8. The method of claim 7, further comprising compounding a result of (b) or (e) with a sodium chloride solution and a maltodextrin solution at pH of 6.7-7.5 and adjusting said pH to 6.7-7.6.

9. The method of claim 8, further comprising filtering a result of said compounding and lyophilizing a filtrate to obtain an amorphous insulin powder with a pH 6.0-7.6 when reconstituted in deionized water at a concentration of 0.03 g of amorphous insulin powder per 1 ml water.

* * * * *